US006420339B1

(12) United States Patent
Gegg et al.

(10) Patent No.: US 6,420,339 B1
(45) Date of Patent: Jul. 16, 2002

(54) SITE-DIRECTED DUAL PEGYLATION OF PROTEINS FOR IMPROVED BIOACTIVITY AND BIOCOMPATIBILITY

(75) Inventors: Colin Gegg; Olaf Kinstler, both of Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/172,644

(22) Filed: Oct. 14, 1998

(51) Int. Cl.$^7$ .................. A61K 38/18; C07K 14/475
(52) U.S. Cl. .................. 514/12; 514/2; 514/909; 530/350; 530/402
(58) Field of Search .................. 530/350, 402–406; 514/2, 8, 12, 909

(56) References Cited

U.S. PATENT DOCUMENTS

| | | |
|---|---|---|
| 4,002,531 A | 1/1977 | Royer |
| 4,695,463 A | 9/1987 | Yang et al. |
| 4,695,623 A | 9/1987 | Stabinsky |
| 4,703,008 A | 10/1987 | Lin |
| 4,766,106 A * | 8/1988 | Katre et al. |
| 4,810,643 A | 3/1989 | Souza |
| 4,897,471 A | 1/1990 | Stabinsky |
| 4,904,584 A | 2/1990 | Shaw |
| 4,999,291 A | 3/1991 | Souza |
| 5,075,222 A | 12/1991 | Hannum et al. |
| 5,166,322 A * | 11/1992 | Shaw et al. |
| 5,372,808 A | 12/1994 | Blatt et al. |
| 5,441,868 A | 8/1995 | Lin |
| 5,521,283 A | 5/1996 | DiMarchi et al. |
| 5,525,705 A | 6/1996 | DiMarchi et al. |
| 5,532,336 A | 7/1996 | DiMarchi et al. |
| 5,541,293 A | 7/1996 | Stabinsky |
| 5,547,933 A | 8/1996 | Lin |
| 5,552,522 A | 9/1996 | DiMarchi et al. |
| 5,552,523 A | 9/1996 | Basinski et al. |
| 5,552,524 A | 9/1996 | Basinski et al. |
| 5,554,727 A | 9/1996 | Basinski et al. |
| 5,559,208 A | 9/1996 | Basinski et al. |
| 5,563,243 A | 10/1996 | DiMarchi et al. |
| 5,563,244 A | 10/1996 | DiMarchi et al. |
| 5,563,245 A | 10/1996 | DiMarchi et al. |
| 5,567,678 A | 10/1996 | DiMarchi et al. |
| 5,567,803 A | 10/1996 | Basinski et al. |
| 5,569,743 A | 10/1996 | DiMarchi et al. |
| 5,569,744 A | 10/1996 | Basinski et al. |
| 5,574,133 A | 11/1996 | DiMarchi et al. |
| 5,580,954 A | 12/1996 | DiMarchi et al. |
| 5,581,476 A | 12/1996 | Osslund |
| 5,582,823 A | 12/1996 | Souza |
| 5,594,101 A | 1/1997 | Becker et al. |
| 5,594,104 A | 1/1997 | Basinski et al. |
| 5,605,886 A | 2/1997 | Basinski et al. |
| 5,614,379 A | 3/1997 | MacKellar |
| 5,618,698 A | 4/1997 | Lin |
| 5,621,080 A | 4/1997 | Lin |

(List continued on next page.)

FOREIGN PATENT DOCUMENTS

| | | |
|---|---|---|
| EP | 0 539 167 A2 | 4/1993 |
| EP | 0 725 078 A1 | 8/1996 |
| EP | 0 725 079 A1 | 8/1996 |
| EP | 0 736 599 A2 | 10/1996 |
| EP | 0 741 187 A2 | 11/1996 |
| EP | 0 744 408 A2 | 11/1996 |
| EP | 0 745 610 A2 | 12/1996 |
| EP | 0 822 199 A2 | 2/1998 |
| EP | 0 835 879 A2 | 4/1998 |
| WO | WO 91/05795 | 5/1991 |
| WO | WO 92/17505 | 10/1992 |
| WO | WO 94/17185 | 8/1994 |
| WO | WO 95/17206 | 6/1995 |
| WO | WO 96/05309 | 2/1996 |
| WO | WO 96/22308 | 7/1996 |
| WO | WO 96/23513 | 8/1996 |
| WO | WO 96/23514 | 8/1996 |
| WO | WO 96/23515 | 8/1996 |
| WO | WO 96/23516 | 8/1996 |
| WO | WO 96/23517 | 8/1996 |

(List continued on next page.)

OTHER PUBLICATIONS

Barinaga, M., " "Obese" Protein Slims Mice", Science, vol. 269, pp. 475–476, (1995).

Bendele, et al., "Short Communication: Renal Tubular Vacuolation in Animals Treated with Polyethylene–Glycol–Conjugated Proteins", Toxicological Sciences, vol. 42, pp. 152–157, (1998).

Campfield, et al., "Recombinant Mouse OB Protein: Evidence for a Peripheral Signal Linking Adiposity and Central Neural Networks", Science, vol. 269, pp. 546–549, (1995).

Conover, et al., "Physiological Effect of Polyethylene Glycol Conjugation on Stroma–Free Bovine Hemoglobin in the Conscious Dog After Partial Exchange Transfusion", Artificial Organs, vol. 21(5), pp. 369–378, (1997).

Creighton, T., "Proteins Structures and Principles", W.H. Freeman and Co., New York,(1984).

Ford, et al., "Fusion Tails for the Recovery and Purification of Recombinant Proteins", Protein Expression and Purification, vol. 2, pp. 95–107, (1991).

(List continued on next page.)

Primary Examiner—Christine J. Saoud
(74) Attorney, Agent, or Firm—Craig A. Crandall; Ron K. Levy; Steven M. Odre

(57) ABSTRACT

The present invention relates generally to the chemical modification of biologically active agents. More, specifically, the invention relates to a novel approach to engineer, through mutagenesis and site-directed chemical conjugation, specific, well-defined dualPEGylated-protein bioconjugates, consisting of two polyethylene glycol (PEG) macromolecules chemically conjugated to the protein at two specifically defined amino acid residues. The described dualPEGylated-protein bioconjugates show substantially improved bioefficacy and biocompatibility.

4 Claims, 7 Drawing Sheets

U.S. PATENT DOCUMENTS

| | | | |
|---|---|---|---|
| 5,691,309 A | | 11/1997 | Basinski et al. |
| 5,719,266 A | | 2/1998 | DiMarchi et al. |
| 5,935,810 A | * | 8/1999 | Friedman et al. |
| 6,001,968 A | * | 12/1999 | Friedman et al. |
| 6,025,324 A | * | 2/2000 | Bailon et al. |
| 6,025,325 A | * | 2/2000 | Campfield et al. |
| 6,048,837 A | * | 4/2000 | Friedman et al. |

FOREIGN PATENT DOCUMENTS

| | | |
|---|---|---|
| WO | WO 96/23518 | 8/1996 |
| WO | WO 96/23519 | 8/1996 |
| WO | WO 96/23520 | 8/1996 |
| WO | WO 96/23815 | 8/1996 |
| WO | WO 96/27385 | 9/1996 |
| WO | WO 96/31526 | 10/1996 |
| WO | WO 96/34111 | 10/1996 |
| WO | WO 96/34885 | 11/1996 |
| WO | WO 96/35787 | 11/1996 |
| WO | WO 96/37517 | 11/1996 |
| WO | WO 96/40912 | 12/1996 |
| WO | WO 97/00128 | 1/1997 |
| WO | WO 97/00886 | 1/1997 |
| WO | WO 97/01010 | 1/1997 |
| WO | WO 97/01331 | 1/1997 |
| WO | WO 97/06816 | 2/1997 |
| WO | WO 97/16550 | 5/1997 |
| WO | WO 97/18833 | 5/1997 |
| WO | WO 97/20933 | 6/1997 |
| WO | WO 97/23614 | 7/1997 |
| WO | WO 97/38014 | 10/1997 |
| WO | WO 97/46585 | 12/1997 |
| WO | WO 98/08512 | 4/1998 |
| WO | WO 98/24896 | 6/1998 |
| WO | WO 98/28427 | 7/1998 |
| WO | WO 00/09165 | 2/2000 |

OTHER PUBLICATIONS

Friedman, J., "The Alphabet of Weight Control", Nature, vol. 385, pp. 119–120, (1997).

Halaas, et al., "Weight–Reducing Effects of the Plasma Protein Encoded by the obese Gene", Science, vol. 269, pp. 543–546, (1995).

Murakami, et al., "Cloning of Rat Obese cDNA and its Expression in Obese Rats", Biochemical and Biophysical Research Communications, vol. 209(3), pp. 944–952, (1995).

Pelleymounter, et al., "Effects of the obese Gene Product on Body Weight Regulation in ob/ob Mice", Science, vol. 269, pp. 540–543, (1995).

Young, et al., "Characterization of the Receptor Binding Determinants of Granulocyte Colony Stimulating Factor", Protein Science, vol. 6, pp. 1228–1236, (1997).

* cited by examiner

SEQUENCE LISTING

<160> NUMBER OF SEQ ID NOS: 7

<210> SEQ ID NO 1
<211> LENGTH: 146
<212> TYPE: PRT
<213> ORGANISM: Human Leptin -continued

```
<400> SEQUENCE: 1

Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
tccatgccgt cctgtaacgt tatccagatc                                    30

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:  Synthetic
      Oligonucleotide

<400> SEQUENCE: 3
gatctggata acgttacagg acggcatgga g                                  31

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:  Synthetic
      Oligonucleotide

<400> SEQUENCE: 4
gttatccaga tctgtaacga cctggagaac                                    30

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:  Synthetic
      Oligonucleotide
```

```
<400> SEQUENCE: 5
gttctccagg tcgttacaga tctggata                                                  28

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:  Synthetic
      Oligonucleotide

<400> SEQUENCE: 6
aacataagta cctgtaggat cg                                                        22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:  Synthetic
      Oligonucleotide

<400> SEQUENCE: 7
gttattgctc agcggtggca                                                           20
```

SITE-DIRECTED DUAL PEGYLATION OF PROTEINS FOR IMPROVED BIOACTIVITY AND BIOCOMPATIBILITY

FIELD OF THE INVENTION

The present invention relates to a novel approach to engineer, through mutagenesis and site-directed chemical conjugation, specific, well-defined dualPEGylated-protein bioconjugates, consisting of two polyethylene glycol (PEG) macromolecules chemically conjugated to the protein at two specifically defined amino acid residues. The described dualPEGylated-protein bioconjugates show substantially improved bioefficacy and biocompatibility.

BACKGROUND OF THE INVENTION

Due to recent advances in genetic and cell engineering technologies, proteins known to exhibit various pharmacological actions in vivo are capable of production in large amounts for pharmaceutical applications. Such proteins include erythropoietin (EPO), granulocyte colony-stimulating factor (G-CSF), interferons (alpha, beta, gamma, consensus), tumor necrosis factor binding protein (TNFbp), interleukin-1 receptor antagonist (IL-1ra), brain-derived neurotrophic factor (BDNF), kerantinocyte growth factor (KGF), stem cell factor (SCF), megakaryocyte growth differentiation factor (MGDF), osteoprotegerin (OPG), glial cell line derived neurotrophic factor (GDNF) and obesity protein (OB protein). OB protein may also be referred to herein as leptin.

Leptin is active in vivo in both ob/ob mutant mice (mice obese due to a defect in the production of the OB gene product) as well as in normal, wild type mice. The biological activity manifests itself in, among other things, weight loss. See generally, Barinaga, "Obese" Protein Slims Mice, *Science*, 269:475–476 (1995) and Friedman, "The Alphabet of Weight Control," *Nature*, 385:119–120 (1997). It is known, for instance, that in ob/ob mutant mice, administration of leptin results in a decrease in serum insulin levels, and serum glucose levels. It is also known that administration of leptin results in a decrease in body fat. This was observed in both ob/ob mutant mice, as well as non-obese normal mice. Pelleymounter et al., *Science*, 269:540–543 (1995); Halaas et al., *Science*, 269:543–546 (1995). See also, Campfield et al., *Science*, 269:546–549 (1995) (Peripheral and central administration of microgram doses of leptin reduced food intake and body weight of ob/ob and diet-induced obese mice but not in db/db obese mice.) The OB protein, analogs, derivatives and use thereof as modulators for the control of weight and adiposity of animals, including mammals and humans, has been disclosed in greater detail in WO 96/05309, supra. See also, PCT International Publication Numbers WO 96/40912, WO 97/06816, 97/18833, WO 97/38014, WO 98/08512 and WO 98/28427. The OB protein, or leptin, as it is called herein, causes weight loss in humans; Greenberg et al., "Preliminary safety and efficacy of recombinant methionyl human leptin (rL) administered by SC injection in lean and obese subjects." Poster presented at: 58th Annual Meeting and Scientific Sessions of the American Diabetes Association; Jun. 14, 1998; Chicago, Ill. In none of these reports have toxicities been observed, even at the highest doses.

Preliminary leptin induced weight loss experiments in animal models predict the need for a high concentration leptin formulation with chronic administration to effectively treat human obesity. Dosages in the milligram protein per kilogram body weight range, such as 0.5 or 1.0 mg/kg/day or below, are desirable for injection of therapeutically effective amounts into larger mammals, such as humans. An increase in protein concentration is thus necessary to avoid injection of large volumes, which can be uncomfortable or possibly painful to the patient.

Unfortunately, for preparations of a pharmaceutical composition for injection in humans, it has been observed that the leptin amino acid sequence is insoluble at physiologic pH at relatively high concentrations, such as above about 2 mg active protein/milliliter of liquid. The poor solubility of leptin under physiological conditions appears to contribute to the formation of leptin precipitates at the injection site in a concentration dependent manner when high dosages are administered in a low pH formulation. Associated with the observed leptin precipitates is an inflammatory response at the injection site which includes a mixed cell infiltrate characterized by the presence of eosinophils, macrophages and giant cells.

To date, there have been no reports of stable preparations of human OB protein at concentrations of at least about 2 mg/ml at physiologic pH, and further, no reports of stable concentrations of active human OB protein at least about 50 mg/ml or above. The development of leptin forms which would allow for high dosage without the aforementioned problems would be of great benefit. It is therefore one object of the present invention to provide improved forms of leptin by way of site-specific chemical modification of the protein.

There are several methods of chemical modification of useful therapeutic proteins which have been reported. For example, there is a long history of proteins chemically modified with polyethylene glycol demonstrating improved pharmacological properties. Among these properties are increased serum half-life, improved solubility and decreased immunogenicity. Chemical modification with a single 20 kDa polyethylene glycol (PEG) polymer at the N-terminus of leptin results in a highly efficacious molecule which demonstrates substantial dose reduction and increased solubility relative to the unmodified native protein; see, e.g., PCT WO 96/40912, supra, at page 8 et seq. for a description of N-terminally derivatizing leptin (therein referred to as OB Protein). Although the PEG polymer extends the circulating half-life of the bioconjugate and may impart some reduced immunogenicity, it has also been found to accumulate in kidney vacoules when administered regularly at a high dose (10 mg/kg). This phenomena has been reported with other PEGylated protein preparations; see e.g., Conover et al., *Artificial Organs*, 21(5):369–378 (1997); Bendele et al., *Toxicological Sciences*, 42:152 (1997). Although it is not known if such vacuoles are detrimental to the health of an individual, it is preferable that drug administration have no associated anatomical abnormalities.

It was thus an object of the present invention to produce a leptin conjugate sufficiently large to escape glomerular filtration by the kidneys, and thus demonstrate little or no propensity to induce kidney vacuolation. Production of such conjugates is achieved using a course of rational mutagenesis combined with the site-directed dual PEGylation of leptin with appropriately sized polymers. Importantly, unlike the current strategies for poly-PEGylation of proteins, which result in heterogeneous mixtures of positional isoforms which are hard to separate and which vary in intrinsic bioactivity, the dualPEGylated protein bioconjugates of the present invention contain specific conjugation sites which were engineered to provide homogenous preparations which maintain the intrinsic bioactivity of the conjugate while exploiting the pharmacokinetic advantages of PEGylated-protein conjugates.

SUMMARY OF THE INVENTION

The present invention relates to substantially homogenous preparations of chemically modified proteins, e.g. leptin, and methods therefor. Unexpectedly, site-specific chemical modification of leptin demonstrated advantages in bioavailibility and biocompatibility which are not seen in other leptin species. Importantly, the methods described herein are broadly applicable to other proteins (or analogs thereof), as well as leptin. Thus, as described below in more detail, the present invention has a number of aspects relating to chemically modifying proteins (or analogs thereof) as well as specific modifications of specific proteins.

In one aspect, the present invention relates to a substantially homogenous preparation of dualPEGylated-leptin (or analog thereof) and related methods. Importantly, the method described results in a high yield of dualPEGylated protein which is modified exclusively at two defined sites, thereby providing processing advantages as compared to other species involving random modification. The present invention stems from the observation that, as compared to unaltered native recombinant human leptin, dualPEGylated-recombinant human leptin has substantially improved bioactivity and biocompatibility.

It has been found, surprisingly and importantly, that dualPEGylated-leptin bioconjugates prepared from 20 kDa, 30 kDa, and 40 kDa PEG polymers, proved highly efficacious, and demonstrated little or no propensity for kidney vacuolation. Significantly, when the dualPEGylated-leptin bioconjugates were administered in a single dose, weight loss was maintained for over 7 days, at twice the level of an equivalent dose of unmodified leptin dosed daily over the 7 day period.

The recombinant human leptin used in the working examples below was first modified such that select cysteine mutations were engineered into the leptin protein sequence. The resultant recombinant human leptin analogs were recoverable in high yield and then used to prepare the dualPEGylated bioconjugates. Thus, in one aspect, the present invention relates to human leptin having cysteine mutations engineered into positions 72 or 78 of the leptin protein sequence.

The present invention also relates to dualPEGylated human leptin bioconjugates wherein PEG is conjugated at the N-terminus and at position 78 of the leptin protein sequence. Preferably the PEG has a molecular weight from about 10 kDa to about 100 kDa. A particularly preferred PEG is about 20 kDa for each polymer chain.

The present invention further relates to all of the dualPEGylated human leptin bioconjugates as above, in a pharmaceutically acceptable carrier.

The present invention further relates to processes for preparing dualPEGylated protein bioconjugates as above. The principal embodiment of the method for making the substantially homogenous preparation of dualPEGylated-protein comprises: (a) engineering a cysteine residue into a specific amino acid position within the amino acid sequence of said protein to provide an analog of said protein; (b) conjugating a polyethylene glycol to said analog at said cysteine residue to provide a monoPEGylated protein conjugate; (c) conjugating a second polyethylene glycol to the N-terminus of said conjugate to provide a dualPEGylated bioconjugate; and (d) isolating said dualPEGylated bioconjugate.

The present invention also relates to methods of treatment of individuals using dualPEGylated human leptin bioconjugates as above.

DETAILED DESCRIPTION OF THE INVENTION

The present invention relates to substantially homogenous preparations of chemically modified proteins, and methods therefor. "Substantially homogenous" as used herein means that the only chemically modified proteins observed are those having one "modifier" (e.g., PEG) moiety. The preparation may contain unreacted (i.e., lacking modifier moiety) protein. As ascertained by peptide mapping and N-terminal sequencing, one example below provides for a preparation which is at least 90% modified protein, and at most 10% unmodified protein. Preferably, the chemically modified material is at least 95% of the preparation and most preferably, the chemically modified material is 99% of the preparation or more.

The chemically modified material has biological activity. The present "substantially homogenous" dualPEGylated-leptin preparations provided herein are those which are homogenous enough to display the advantages of a homogenous preparation, e.g., ease in clinical application in predictability of lot to lot pharmacokinetics.

As used herein, biologically active agents refers to recombinant or naturally occurring proteins, whether human or animal, useful for prophylactic, therapeutic or diagnostic application. The biologically active agent can be natural, synthetic, semi-synthetic or derivatives thereof. In addition, biologically active agents of the present invention can be perceptible. A wide range of biologically active agents are contemplated. These include but are not limited to hormones, cytokines, hematopoietic factors, growth factors, antiobesity factors, trophic factors, anti-inflammatory factors, and enzymes (see also U.S. Pat. No. 4,695,463 for additional examples of useful biologically active agents). One skilled in the art will readily be able to adapt a desired biologically active agent to the compositions of present invention.

Such proteins would include but are not limited to interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,810,643, 4,999,291, 5,581,476, 5,582,823, and PCT Publication No. 94/17185, hereby incorporated by reference including drawings), stem cell factor (PCT Publication Nos. 91/05795, 92/17505 and 95/17206, hereby incorporated by reference including drawings), osteoprotegerin (PCT Publication No. 97/23614, hereby incorporated by reference including drawings) and leptin (OB protein).

Figure 3:
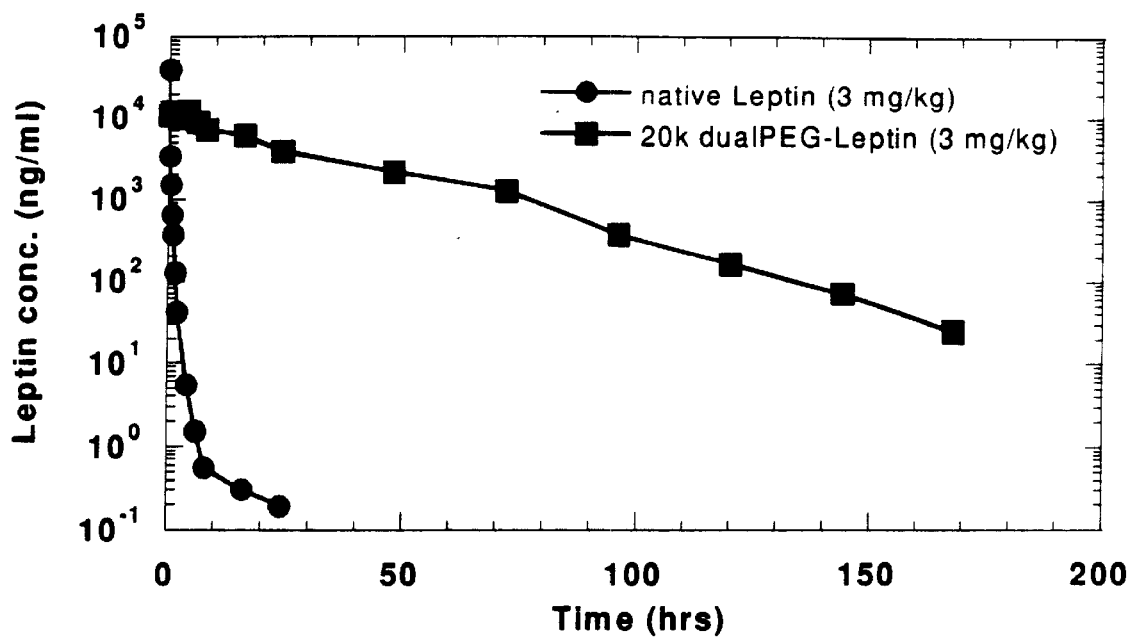
FIG. 3 is a graph depicting the pharmacokinetic profiles for 20 kDa dualPEGylated-leptin in mice following intravenous injections of a single 3 mg/kg dose. Leptin concentration (ng/mL) is plotted vs. time (hrs).

The type of leptin used for the present dualPEGylated-leptin preparations may be selected from those described in PCT International Publication Number WO 96/05309, as cited above and herein incorporated by reference in its entirety. FIG. 3 of that publication (as cited therein SEQ ID NO: 4) depicts the full deduced amino acid sequence derived for human leptin (referred to as the human "OB" protein). The amino acids are numbered from 1 to 167. A signal sequence cleavage site is located after amino acid 21 (Ala) so that the mature protein extends from amino acid 22 (Val) to amino acid 167 (Cys). For the present disclosure, a different numbering is used herein, where the amino acid position 1 is the valine residue which is at the beginning of the mature protein. The amino acid sequence for mature, recombinant methionyl human leptin is presented herein as SEQ ID NO: 1, where the first amino acid of the mature protein is valine (at position 1) and a methionyl residue is located at position —1 (not included in the sequence below).

```
                                          SEQ ID NO: 1
       V P I Q K V Q D D T K T L I K T I V

T R I N D I S H T Q S V S S K Q K V T G

L D F I P G L H P I L T L S K M D Q T L

A V Y Q Q I L T S M P S R N V I Q I S N

D L E N L R D L L H V L A F S K S C H L

P W A S G L E T L D S L G G V L E A S G

Y S T E V V A L S R L Q G S L Q D M L W

Q L D L S P G C
```

However, as with any of the present leptin moieties, the methionyl residue at position −1 may be absent.

Alternatively, one may use a natural variant of human leptin, which has 145 amino acids and, as compared to rmetHu-leptin of SEQ ID NO: 1, has a glutamine absent at position 28.

Generally, the leptin moiety for human pharmaceutical use herein will be capable of therapeutic use in humans (see also, animal leptins, below). Thus, one may empirically test activity to determine which leptin moieties may be used. As set forth in WO 96/05309, leptin protein in its native form, or fragments (such as enzyme cleavage products) or other truncated forms and analogs may all retain biological activity. Any of such forms may be used as a leptin moiety for the present dualPEGylated-leptin conjugates, although such altered forms should be tested to determine desired characteristics. See also, PCT International Publication Numbers WO 96/40912, WO 97/06816, 97/18833, WO 97/38014, WO 98/08512 and WO 98/28427, herein incorporated by reference in their entireties.

One may prepare an analog of recombinant human leptin by altering amino acid residues in the recombinant human sequence, such as substituting the amino acids which diverge from the murine sequence. Murine leptin is substantially homologous to human leptin, particularly as a mature protein and, further, particularly at the N-terminus. Because the recombinant human protein has biological activity in mice, such an analog would likely be active in humans. For example, in the amino acid sequence of native human leptin as presented in SEQ ID NO: 1, one may substitute with another amino acid one or more of the amino acids at positions 32, 35, 50, 64, 68, 71, 74, 77, 89, 97, 100, 101, 105, 106, 107, 108, 111, 118, 136, 138, 142 and 145. One may select the amino acid at the corresponding position of the murine protein (see Zhang et al., 1994, supra) or another amino acid.

One may further prepare "consensus" molecules a based on the rat OB protein sequence. Murakami et al., *Biochem. Biophys. Res. Comm.*, 209:944–52 (1995) herein incorporated by reference. Rat OB protein differs from human OB protein at the following positions (using the numbering of SEQ ID NO: 1): 4, 32, 33, 35, 50, 68, 71, 74, 77, 78, 89, 97, 100, 101, 102, 105, 106, 107, 108, 111, 118, 136, 138 and 145. One may substitute with another amino acid one or more of the amino acids at these divergent positions. The positions underlined are those in which the murine OB protein as well as the rat OB protein are divergent from the human OB protein and, thus, are particularly suitable for alteration. At one or more of the positions, one may substitute an amino acid from the corresponding rat OB protein, or another amino acid.

The positions from both rat and murine OB protein which diverge from the mature human OB protein are: 4, 32, 33, 35, 50, 64, 68, 71, 74, 77, 78, 89, 97, 100, 101, 102, 105, 106, 107, 108, 111, 118, 136, 138, 142 and 145. An OB protein according to SEQ ID NO: 1 having one or more of the above amino acids replaced with another amino acid, such as the amino acid found in the corresponding rat or murine sequence, may also be effective.

In addition, the amino acids found in rhesus monkey OB protein which diverge from the mature human OB protein are (with identities noted in parentheses in one letter amino acid abbreviation): 8 (S), 35 (R), 48 (V), 53 (Q), 60 (I), 66 (I), 67 (N), 68 (L), 89 (L), 100 (L), 108 (E), 112 (D) and 118 (L). Since the recombinant human OB protein is active in cynomolgus monkeys, a human OB protein according to SEQ ID NO: 1 having one or more of the rhesus monkey divergent amino acids replaced with another amino acid, such as the amino acids in parentheses, may be effective. It should be noted that certain rhesus divergent amino acids are also those found in the above murine and rat species (positions 35, 68, 89, 100, 108 and 118). Thus, one may prepare a murine/rat/rhesus/human consensus molecule (using the numbering of SEQ ID NO: 1 ) having one or more of the amino acids replaced by another amino acid at positions: 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142 and 145. The positions underlined are those in which all three species are divergent from human OB protein. A particularly preferred human leptin analog is one wherein the amino acids at position 100 (Trp) or 138 (Trp), and more preferably, both positions are substituted with another amino acid, preferably Gln.

Other analogs may be prepared by deleting a part of the protein amino acid sequence. For example, the mature protein lacks a leader sequence (−22 to −1). One may prepare the following truncated forms of human OB protein molecules (using the numbering of SEQ ID NO: 1):

(i) amino acids 98–146;
(ii) amino acids 1–99 and (connected to) 112–146;
(iii) amino acids 1–99 and (connected to) 112–146 having one or more of amino acids 100–111 sequentially placed between amino acids 99 and 112.

In addition, the truncated forms may also have altered one or more of the amino acids which are divergent (in the murine, rat or rhesus OB protein) from human OB protein. Furthermore, any alterations may be in the form of altered amino acids, such as peptidomimetics or D-amino acids.

Also included are those proteins as set forth above with amino acid substitutions which are "conservative" according to acidity, charge, hydrophobicity, polarity, size or any other characteristic known to those skilled in the art. These are set forth in Table 1, below. See generally, Creighton, Proteins, passim (W. H. Freeman and Company, N.Y., 1984); Ford et al., *Protein Expression and Purification* 2:95–107 (1991), which are herein incorporated by reference.

TABLE 1

Conservative Amino Acid Substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Therefore, the present dualPEGylated-leptin conjugates may be selected from among (according to the amino acid sequence as presented in SEQ ID NO: 1 herein):

(a) the amino acid sequence of SEQ ID NO: 1, optionally lacking a glutaminyl residue at position 28, and further optionally having a methionyl residue at the N-terminus;
(b) an amino acid sequence of subpart (a) having a different amino acid substituted in one or more of the following positions: 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142 and 145;
(c) an amino acid sequence of subpart (b) wherein the amino acids at positions 100 and 138 are substituted with Gln;
(d) a truncated leptin protein analog selected from among:
  (i) amino acids 98–146
  (ii) amino acids 1–99 and 112–146
  (iii) amino acids 1–99 and 112–146 having one or more of amino acids 100–111 sequentially placed between amino acids 99 and 112; and,
  (iv) the truncated leptin analog of subpart (i) having one or more of amino acids 100, 102, 105, 106, 107, 108, 111, 112, 118, 136, 138, 142 and 145 substituted with another amino acid;
  (v) the truncated leptin analog of subpart (iii) having one or more of amino acids 4, 8, 32, 33, 35, 48, 50, 53, 60, 64, 66, 67, 68, 71, 74, 77, 78, 89, 97, 112, 118, 136, 138, 142 and 145 replaced with another amino acid;
  (vi) the truncated leptin analog of subpart (iv) having one or more of amino acids 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142 and 145 replaced with another amino acid; and
  (vii) the truncated leptin analog of any of subparts (i)–(vi) having an N-terminal methionyl residue;
(e) a leptin protein of any of subparts (a)–(d) having one or more conserved amino acid substitutions.

Leptin proteins, analogs and related molecules are also reported in the following publications; however, no representation is made with regard to the activity of any composition reported: U.S. Pat. Nos. 5,521,283; 5,525,705; 5,532,336; 5,552,522; 5,552,523; 5,552,524; 5,554,727; 5,559,208; 5,563,243; 5,563,244; 5,563,245; 5,567,678; 5,567,803; 5,569,743; 5,569,744; 5,574,133; 5,580,954; 5,594,101; 5,594,104; 5,605,886; 5,614,379; 5,691,309; 5,719,266 (Eli Lilly and Company); PCT WO96/23513; WO96/23514; WO96/23515; WO96/23516; WO96/23517; WO96/23518; WO96/23519; WO96/23520; WO96/23815; WO96/27385; WO96/34111; WO96/37517; WO97/00886; EP 725078; EP 725079; EP 744408; EP 745610; EP 835879 (Eli Lilly and Company); PCT WO96/22308 (Zymogenetics); PCT WO96/31526 (Amylin Pharmaceuticals, Inc.); PCT WO96/34885; WO97/46585 (Smithkline Beecham PLC); PCT WO96/35787 (Chiron Corporation); PCT WO97/16550 (Bristol-Myers Squibb); PCT WO97/20933 (Schering Corporation) EP 736599 (Takeda); EP 741187 (F. Hoffman LaRoche).

To the extent these references provide for useful leptin proteins or analogs, or associated compositions or methods, such compositions and/or methods may be used in conjunction with the present dualPEGylated-leptin conjugates, such as for co-administration (together or separately, in a selected dosage schedule). With the above provisos, these publications are herein incorporated by reference.

In addition, biologically active agents can also include but are not limited to insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase and kallikrein. The term proteins, as used herein, includes peptides, polypeptides, consensus molecules, analogs, derivatives or combinations thereof.

Whatever the protein (or analog thereof) used, said protein will be modified such that a select cysteine mutation is engineered into the protein sequence. The purpose of the cysteine point mutation is to allow a second conjugation site which compliments preexisting technology for PEG conjugation specifically to the N-terminus. These "cysteine" protein analogs can be easily prepared using coventional methods well known to one of ordinary skill in the art.

For example, granulocyte colony stimulating factor (GCSF) is a 4-helix bundle protein very similar in structure to leptin. While GCSF is readily monoPEGylated at the N-terminus by reductive alkylation, additional amine specific PEGylations occur randomly at any of the four lysine residues ($Lys^{16}$, $Lys^{23}$, $Lys^{34}$ and $Lys^{40}$). This results in heterogeneous preparations of diPEGylated-GCSF composed of a mixture of at least 4 different positional isoforms. With difficulty, these positional isoforms can be isolated and have demonstrated broadly varying degree's of residual activity. An attempt to topographically map the GCSF active site by alanine scanning identified at least 6 residues ($Lys^{16}$, $Glu^{19}$, $Lys^{46}$, $Glu^{46}$, $Asp^{109}$ and $Asp^{112}$) residing on helices #1 & 4, which when mutated to alanine resulted in >5-fold loss in GCSF activity (Young, et al, *Prot. Sci.*, 6:1228–1236 (1997). This would support the observation that PEGylation at $Lys^{16}$ or $Lys^{23}$ results in diminished GCSF activity. To apply dualPEGylation technology to GCSF a cysteine residue would have to be engineered in a site which is distal to both the active site and the N-terminus. Such a cysteine mutation would preferentially be placed on the surface of an element of secondary structure, be solvent exposed, but not overly accessible to intermolecular disulphide formation. Proposed as examples of this approach are the mutations $Ser^{53} \to Cys^{53}$, $Gly^{87} \to Cys^{87}$ and $Ser^{155} \to Cys^{155}$ on helices #2, 3 & 5 respectively. Noting however that any other position may be judged suitable if it preserves GCSF activity, promotes effective PEG conjugation while discouraging intermolecular protein crosslinking and can be produced in high yield.

In the case of certain proteins, one may alternatively use a cysteine residue already present in the native sequence as one site for PEGylation, thus avoiding PEGylation at the N-terminus. Additionally, one could engineer two select cysteine mutations into the native protein sequence and then use each of those cysteine residues in the dualPEgylation conjugation, again avoiding PEGylation at the N-terminus.

Leptin analogs prepared in the present invention include select cysteine mutations, $Arg^{72} \to Cys^{72}$ or $Ser^{78} \to Cys^{78}$. These mutations were based on topographically mapping small chemical modifications to a three-dimensional model of leptin and correlating those modifications to their impact on in vitro and in vivo activity of the protein. The sites were selected both to preserve the intrinsic bioactivity of leptin and to allow alternate but compatible chemistries which permit discrimination between the two sites (i.e. the N-terminus and the second cysteine site), thus providing for independent variation of PEG sizes and conformations at either site. Additional considerations were given to positioning the mutations distal to the N-terminus and on a solvent exposed surface to promote crosslinking chemistries.

Mutation $Arg^{72} \to Cys^{72}$ was placed in a flexible loop to improve solvent accessibility, whereas mutation $Ser^{78} \to Cys^{78}$ occurs at the bottom of helix C where it might enhance refold recovery by being juxtaposed away from the native cysteines ($Cys^{97}$ and $Cys^{147}$) during the early phases of refolding. The new $Cys^{78}$ conjugation site is both distal to the N-terminus and the putative receptor binding interface. Thus positioned, $Cys^{78}$ was postulated to help minimize steric interference with both second polymer conjugation and receptor binding while maximizing the hydrodynamic volume of the conjugate. In addition, the $Cys^{78}$ site was selected because of its location in helix C, from where it is proposed to resist spontaneous inter- or intra-disulphide formation thus improving analog stability and process recovery. This hypothesis is supported by $Arg^{72} \to Cys^{72}$ analog which was produced at the same time. The $Arg^{72} \to Cys^{72}$ site is in an adjacent flexible loop and when expressed in *E. coli* was almost unrecoverable due to high levels of aggregates and misfolds.

Because the two conjugation chemistries are mutually compatible and relatively site-specific, the resultant conjugates typically have a high degree of homogeneity and are readily purified by conventional chromatographic methods.

The "cysteine" protein analogs described above are then used to prepare the dualPEGylated-proteiin bioconjugates. DualPEGylated-leptin bioconjugates prepared in the present invention use the $Ser^{78} \to Cys^{78}$ leptin analog in a simple two-step synthesis to produce the desired dualPEGylated-leptin bioconjugate. The resultant bioconjugate has the leptin analog PEGylated at opposite ends of the 4-helix bundle by site-directed coupling at $Cys^{78}$ and the N-terminus.

The polymer molecules used may be selected from among water soluble polymers. (For the reductive alkylation procedure, the polymers should have a single reactive aldehyde.) The polymer selected should be water soluble so that the protein to which it is attached does not precipitate in an aqueous environment, such as a physiological environment. For reductive alkylation, the polymer selected should have a single reactive aldehyde so that the degree of polymerization may be controlled as provided for in the present methods. The polymer may be branched or unbranched. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. The water soluble polymer may be selected from the group consisting of, for example, polyethylene glycol, dextran or poly(n-vinyl pyrrolidone)polyethylene glycol, propropylene glycol homopolymers, prolypropylene oxide/ethylene oxide co-polymers, polyoxyethylated polyols and polyvinyl alcohol.

Subject to considerations for optimization as discussed below, the polymer may be of any molecular weight, and may be branched or unbranched. For polyethylene glycol, the preferred molecular weight is between about 10 kDa and about 100 kDa (the term "about" indicating that in preparations of polyethylene glycol, some molecules will weigh more, some less, than the stated molecular weight). Various sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

A variety of means have been used to attach the polyethylene glycol molecules to the protein. Generally, polyethylene glycol molecules are connected to the protein via a reactive group found on the protein. Amino groups, such as those on lysine residues or at the N-terminus, are convenient for such attachment. For example, Royer (U.S. Pat. No. 4,002,531, above) states that reductive alkylation was used for attachment of polyethylene glycol molecules to an enzyme. EP 0 539 167, published Apr. 28, 1993, Wright, "Peg Imidates and Protein Derivatives Thereof" states that peptides and organic compounds with free amino group(s) are modified with an immediate derivative of PEG or related water-soluble organic polymers. U.S. Pat. No. 4,904,584, Shaw, issued Feb. 27, 1990, relates to the modification of the number of lysine residues in proteins for the attachment of polyethylene glycol molecules via reactive amine groups. PCT WO 96/40912, supra, at page 8 et seq. describes a method of N-terminally derivatizing leptin (therein referred to as OB Protein).

In a preferred embodiment of the present invention, the attachment of the PEG molecule to the protein at the cysteine residue involves attaching the PEG molecule to the cysteine residue using a reaction at ~pH 6.5 to maximize selectivity of maleimide for the $Cys^{78}$ thiol over lysine amines (this pH also minimizes thiol oxidation); while the attachment of the second PEG molecule to the N-terminus of the protein involves attaching the PEG molecule to the leptin moiety under reducing conditions to form an amine bond, at a pH sufficiently acidic so that the amino-terminal amine is not yet protonated while the amine groups at other positions on the leptin protein are protonated.

In general, comprehended by the invention are pharmaceutical compositions comprising effective amounts of chemically modified protein, or derivative products, together with pharmaceutically acceptable diluents, preservatives, solubilizers, emulsifiers, adjuvants and/or carriers needed for administration. (See PCT 97/01331 hereby incorporated by reference.) The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs. 1435–1712 (1990)). The pharmaceutical compositions of the present invention may be administered by oral and non-oral preparations (e.g., intramuscular, subcutaneous, transdermal, visceral, IV (intravenous), IP (intraperitoneal), intraarticular, placement in the ear, ICV (intracerebralventricular), IP (intraperitoneal), intraarterial, intrathecal, intracapsular, intraorbital, injectable, pulmonary, nasal, rectal, and uterine-transmucosal preparations).

Therapeutic uses of the compositions of the present invention depend on the biologically active agent used. One skilled in the art will readily be able to adapt a desired biologically active agent to the present invention for its intended therapeutic uses. Therapeutic uses for such agents are set forth in greater detail in the following publications hereby incorporated by reference including drawings. Therapeutic uses include but are not limited to uses for proteins like interferons (see, U.S. Pat. Nos. 5,372,808, 5,541,293, hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,999,291, 5,581,476, 5,582,823, 4,810, 643 and PCT Publication No. 94/17185, hereby incorporated by reference including drawings), stem cell factor (PCT Publication Nos. 91/05795, 92/17505 and 95/17206, hereby incorporated by reference including drawings), and the OB protein (see PCT publication Nos. 96/40912, 96/05309, 97/00128, 97/01010 and 97/06816 hereby incorporated by reference including figures). In addition, the present compositions may also be used for manufacture of one or more medicaments for treatment or amelioration of the conditions the biologically active agent is intended to treat.

One skilled in the art will be able to ascertain effective dosages by administration and observing the desired therapeutic effect. Preferably, the formulation of the conjugate will be such that between about 0.01 µg leptin moiety/kg body weight/day and 10 mg leptin moiety/kg body weight/day will yield the desired therapeutic effect. The effective dosages may be determined using diagnostic tools over time. For example, a diagnostic for measuring the amount of leptin in the blood (or plasma or serum) may first be used to determine endogenous levels of leptin protein. Such diagnostic tool may be in the form of an antibody assay, such as an antibody sandwich assay. The amount of endogenous leptin protein is quantified initially, and a baseline is determined. The therapeutic dosages are determined as the quantification of endogenous and exogenous leptin protein moiety (that is, protein, analog or derivative found within the body, either self-produced or administered) is continued over the course of therapy. The dosages may therefore vary over the course of therapy, with, for example, a relatively high dosage being used initially, until therapeutic benefit is seen, and lower dosages used to maintain the therapeutic benefits.

Therapeutic uses of dualPEGylated-leptin include weight modulation, the treatment or prevention of diabetes, blood lipid reduction (and treatment of related conditions), increasing lean body mass and increasing insulin sensitivity.

Weight Modulation. The present compositions and methods may be used for weight reduction. Viewed another way, the present compositions may be used for maintenance of a desired weight or level of adiposity. As has been demonstrated in murine models (see infra), administration of the present dualPEGylated-leptin conjugates results in weight loss. The body mass lost is primarily of adipose tissue, or fat. Such weight loss can be associated with the treatment of concomitant conditions, such as those below, and therefore constitute a therapeutic application. In addition, cosmetic uses are provided herein if weight modulation is solely for improvement in appearance.

Treatment of Diabetes. The present compositions and methods may be used in the prevention or treatment of Type II diabetes. As Type II diabetes can be correlated with obesity, use of the present invention to reduce weight (or maintain a desired weight, or reduce or maintain an adiposity level) can also alleviate or prevent the development of diabetes. Moreover, even in the absence of dosages sufficient to result in weight loss, the present compositions may be used to prevent or ameliorate diabetes.

Blood Lipid Modulation. The present compositions and methods may be used in the modulation of blood lipid levels. Hyperlipidemia (also called lipemia; dyslipidemia) is the presence of an abnormally large amount of lipids in the circulating blood. Ideally, in situations where solely reduction in blood lipid levels is desired, or where maintenance of blood lipid levels is desired, the dosage will be insufficient to result in weight loss. Thus, during an initial course of therapy of an obese patient, dosages may be administered whereby weight loss and concomitant blood lipid level lowering is achieved. Once sufficient weight loss is achieved, a dosage sufficient to prevent re-gaining weight, yet sufficient to maintain desired blood lipid levels, or other conditions as set forth herein, for example, may be administered. These dosages can be determined empirically, as the effects of leptin protein are reversible. E.g., Campfield et al., *Science,* 269:546–549 (1995) at 547. Thus, if a dosage resulting in weight loss is observed when weight loss is not desired, one would administer a lower dose in order to achieve the desired blood lipid levels, yet maintain the desired weight. See, e.g., PCT Publication WO 97/06816 herein incorporated by reference.

Increasing Lean Mass or Insulin Sensitivity.

Ideally, in situations where solely an increase in lean body mass is desired, the dosage will be insufficient to result in weight loss. Thus, during an initial course of therapy of an obese person, dosages may be administered whereby weight loss and concomitant fat tissue decrease/lean mass increase is achieved. Once sufficient weight loss is achieved, a dosage sufficient to prevent regaining weight, yet sufficient to maintain desired lean mass increase (or prevention of lean mass depletion) may be administered. For increasing an individual's sensitivity to insulin, similar dosage considerations may be taken into account. Lean mass increase without weight loss may be achieved sufficient to decrease the amount of insulin (or, potentially, amylin, amylin antagonists or agonists, or thiazolidinediones, or other potential diabetes treating drugs) an individual would be administered for the treatment of diabetes. For increasing overall strength, there may be similar dosage considerations. Lean mass increase with concomitant increase in overall strength may be achieved with doses insufficient to result in weight loss. Other benefits, such as an increase in red blood cells (and oxygenation in the blood) and a decrease in bone resorption or osteoporosis may also be achieved in the absence of weight loss. See, e.g., PCT Publication No. WO 97/18833 herein incorporated by reference.

Combination Therapies. The present compositions and methods may be used in conjunction with other therapies, such as altered diet and exercise. Other medicaments, such as those useful for the treatment of diabetes (e.g., insulin and possibly amylin, antagonists or agonists thereof, thiazolidinediones (see, e.g., PCT Publication No. WO 98/08512 herein incorporated by reference), or other potential diabetes treating drugs), cholesterol and blood pressure lowering medicaments (such as those which reduce blood lipid levels or other cardiovascular medicaments), activity increasing medicaments (e.g., amphetamines), diuretics (for liquid elimination), and appetite suppressants (such as agents which act on neuropeptide Y receptors or serotonin reuptake inhibitors). Such administration may be simultaneous or may be in seriatim. In addition, the present methods may be used in conjunction with surgical procedures, such as cosmetic surgeries designed to alter the overall appearance of a body (e.g., liposuction or laser surgeries designed to reduce body mass, or implant surgeries designed to increase the appearance of body mass). The health benefits of cardiac surgeries, such as bypass surgeries or other surgeries designed to relieve a deleterious condition caused by blockage of blood vessels by fatty deposits, such as arterial plaque, may be increased with concomitant use of the present compositions and methods. Methods to eliminate gall stones, such as ultrasonic or laser methods, may also be used either prior to, during or after a course of the present therapeutic methods. Furthermore, the present methods may be used as an adjunct to surgeries or therapies for broken bones, damaged muscle, or other therapies which would be improved by an increase in lean tissue mass.

In addition, the present compositions may be used for manufacture of one or more medicaments for treatment or amelioration of the above conditions.

The following examples are offered to more fully illustrate the invention, but are not to be construed as limiting the scope thereof.

EXAMPLE 1

This example describes the preparation of the $Arg^{72} \rightarrow Cys^{72}$ leptin analog and $Ser^{78} \rightarrow Cys^{78}$ leptin analog.

Recombinant methionyl human leptin (rmetHu-leptin) was used for the present experiments. The leptin moieties used herein may be made in prokaryotic or in eukaryotic cells, although, for the leptin moieties used in the working examples below, bacteria is preferred for ease in commercial manufacture. One may further use leptin made in human cells, such as that made by controlling a native or introduced regulatory element which affects the regulation of an endogenous gene encoding the desired protein.

Two analogs of human leptin containing unpaired cysteine residues were expressed and purified from *E. coli* to serve as substrates in the PEGylation reaction. These were the $Arg^{72} \rightarrow Cys^{72}$ leptin analog and the $Ser^{78} \rightarrow Cys^{78}$ leptin analog (mutations relative to amino acid positions in SEQ ID NO: 1). The analogs were constructed by site specific mutagenesis of SEQ ID NO: 1 using standard PCR technology. The mutagenic oligonucleotides used are shown in Table 2 below:

TABLE 2

| | | |
|---|---|---|
| 1735–46 (sense) | TCCATGCCGTCCTGTAACGTTATCCAGATC | SEQ ID NO: 2 |
| 1735–47 (antisense) | GATCTGGATAACGTTACAGGACGGCATGGAG | SEQ ID NO: 3 |
| 1735–48 (sense) | GTTATCCAGATCTGTAACGACCTGGAGAAC | SEQ ID NO: 4 |
| 1735–49 (antisense) | GTTCTCCAGGTCGTTACAGATCTGGATA | SEQ ID NO: 5 |
| 1216–52 | AACATAAGTACCTGTAGGATCG | SEQ ID NO: 6 |
| 1200–54 | GTTATTGCTCAGCGGTGGCA | SEQ ID NO: 7 |

The antisense primer from each pair (1735–47 for $Arg^{72} \rightarrow Cys^{72}$; 1735–49 for $Ser^{78} \rightarrow Cys^{78}$) was used in a PCR reaction with the vector pAMG21 (ATCC # 98113) universal sense primer 1216–52 to generate the 5' end of the leptin gene containing the desired mutation. The sense primer from each pair (1735–46 for Arg$^{72}$→Cys$^{72}$; 1735–48 for Ser$^{78}$→Cys$^{78}$) was used in a PCR reaction with the vector pAMG21 universal antisense primer 1200–54 to generate the 3' end of the leptin gene containing the desired mutation. The two half molecules were then combined in a third PCR reaction using only the universal primers to generate the full length product containing each mutation. Each PCR product was digested with the restriction endonucleases XbaI and BamHI, and then ligated into the vector pAMG21, also digested with XbaI and BamHI.

Ligated DNA was transformed into competent host cells of E. coli strain 2596. E. coli host strain #2596 is an E.coli K-12 strain derived from Amgen strain #393 (ATCC# 202173 is the hsdR– version of this strain). It has been modified to contain both the temperature sensitive lambda repressor cI857s7 in the early ebg region and the lacI$^Q$ repressor in the late ebg region (68 minutes).

Clones were screened for the ability to produce the recombinant protein product and to possess the gene having the correct nucleotide sequence. A single such clone containing the Arg$^{72}$→Cys$^{72}$ mutation was selected and designated Amgen strain #3559, while another containing the Ser$^{78}$→Cys$^{78}$ mutation was designated Amgen strain #3561. Recombinant expression of leptin analogs was performed as has been described, for example, in WO 96/40912, herein incorporated by reference.

EXAMPLE 2

This example describes the preparation of a dualPEGylated-leptin bioconjugate. Starting with the Ser$^{78}$→Cys$^{78}$ leptin analog prepared as described in Example 1, the following two-step process is utilized:

Step 1. The analog is taken to 2–3 mg/ml in 20–50 mM NaHPO$_4$ buffer, 5 mM EDTA, pH 6.5. Methoxy-PEG-maleimide (PEG$_A$) (Shearwater Polymers) is then added to a 1–3 fold molar excess and allowed to react 2–24 hours at 4° C. to conjugate the Cys$^{78}$ site.

Step 2. The pH of the reaction mixture from step 1 is lowered to pH 4–6 and 5–7 fold excess of methoxy-PEG-aldehyde (PEG,) (Shearwater Polymers) is added with sufficient sodium cyanoborohydride (Sigma) to make 15 mM NaBH$_3$CN. This reaction proceeds overnight at 4° C. with stirring. Upon completion, the reaction is dialyzed against 20 mM NaOAc, pH 4, diluted to <1 mg/ml protein concentration, and the pH adjusted to pH 3.5. This material is then purified by cation exchange chromatography using a High Performance Sepharose SP resin (Pharmacia) in 20 mM NaOAc, pH 4, with a 0–200 mM NaCl gradient.

Because of the discriminating conjugation chemistries it is possible to independently vary the polymers attached at either site. Thus far, 20 kDa and 30 kDa linear PEGs and a 40 kDa branched PEG have been evaluated and the resultant conjugates characterized, inter alia, by SDS-PAGE, SEC-HPLC, light scattering, peptide mapping, in vitro receptor binding assay and in vivo bioassay.

EXAMPLE 3

Figure 1:
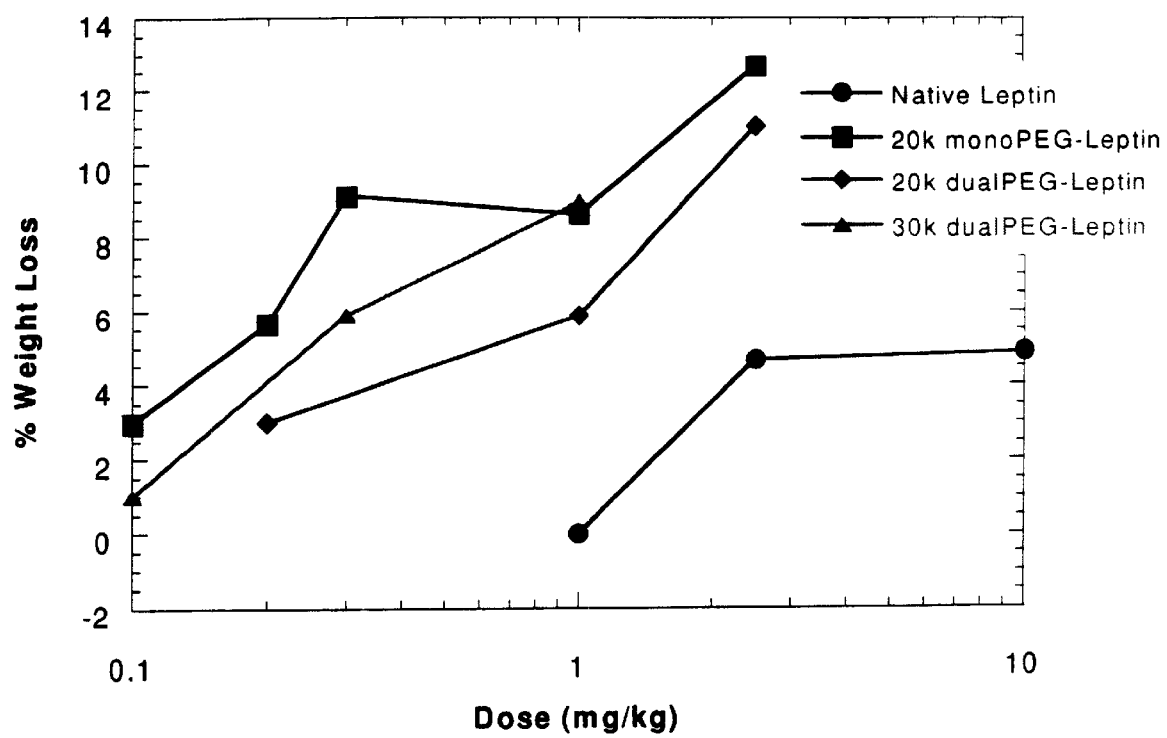
FIG. 1 is a graph depicting various leptin dose response curves in a model wherein mice were dosed daily with 0.1–10 mg/kg protein with subcutaneous administration for 7 days. The curves represent averages of the three greatest weight loss values for each dose from multiple, 7 day, daily dose assays. % weight loss is plotted vs. dose (mg/kg) and % weight loss is calculated as the difference between test group and buffer control.

Dose reductions achieved with the dualPEGylated-leptin bioconjugates were estimated from daily dosing of mice with 0.1–10 mg/kg protein with subcutaneous administration for 7 days. For each conjugate at a given dose the three greatest weight loss values achieved in the course of the 7 day study were averaged. This average weight loss value was then plotted as a function of dose for each dose tested (FIG. 1). The FIG. 1 data demonstrate that dualPEGylated-leptin provides a 13–20 fold dose reduction. Because FIG. 1 includes data from several studies it's defined as a composite dose response curve. Fitting the data for each conjugate to a logarithmic curve provides a linear equation which can be solved to predict the dose required to achieve a certain percentage weight loss. In this case 4% is a mid-range weight loss value that is well represented by the data. Solving for 4% weight loss yields predicted doses and dose reductions relative to native leptin given in Table 3 below.

TABLE 3

| Predicted Dose (mg/kg/day) | Dose Reduction (native/conjugate) | Sample |
|---|---|---|
| 4.4 | N/A | native leptin |
| 0.1 | 44 | 20 kDa monoPEG-leptin |
| 0.33 | 13.3 | 20 kDa dualPEG-leptin |
| 0.21 | 21 | 30 kDa dualPEG-leptin |

EXAMPLE 4

Figure 2:
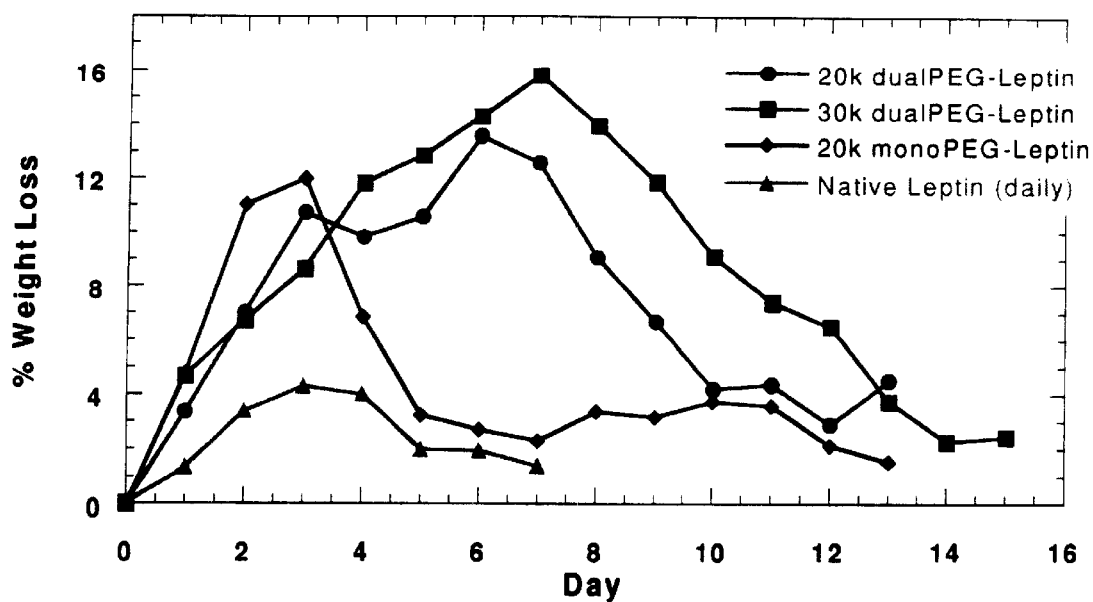
FIG. 2 is a graph depicting single dose induced weight loss percentages for various leptin preparations in a model wherein mice were dosed with a single subcutaneous injection of 10 mg/kg of each preparation. % weight loss is plotted vs. # of days and % weight loss is calculated as the difference between test group and buffer control.

The in vivo efficacy of the dualPEGylated-leptin bioconjugates was tested in wild-type mice by administration of a single, subcutaneous dose at 10 mg/kg and monitoring weight loss relative to a buffer control. As a control the unmodified rhu-leptin was administered daily at 10 mg/kg. Weight loss for the 20 kDa monoPEG-leptin group peaked at 12% in 3 days and was recovered by day 5 (FIG. 2). The 20 kDa dualPEGylated-leptin induced 13% weight loss by day 6 which was recovered by day 10. Even better, the 30 kDa dualPEGylated-leptin induced 16% weight loss by day 7 which was not recovered until day 14. The FIG. 2 data clearly demonstrate that dualPEGylation of leptin promotes substantially increased efficacies which are sustainable from a single dose for up to 14 days. This is an unexpected and enormously beneficial property of dualPEGylated-leptin, as it promises the opportunity to administer single weekly injections of ~10× less total material than native leptin.

EXAMPLE 5

Figure 4:
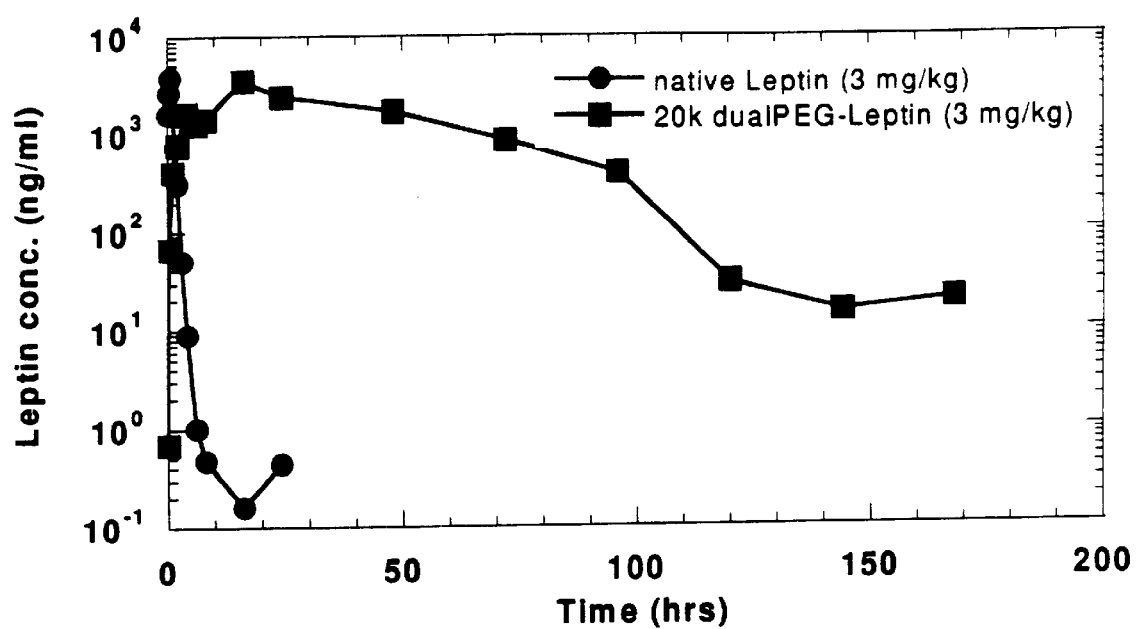
FIG. 4 is a graph depicting the pharmacokinetic profiles for 20 kDa dualPEGylated-leptin in mice following subcutaneous injections of a single 3 mg/kg dose. Leptin concentration (ng/mL) is plotted vs. time (hrs).

Pharmacokinetic profiles for 20 kDa dualPEGylated-leptin were determined in normal mice following subcutaneous or intravenous administration of a single 3 mg/kg dose. The concentration of 20 kDa dualPEGylated-leptin in serum samples taken at regular intervals were determined by ELISA. With intravenous administration, the 20 kDa dualPEG-leptin conjugate quickly achieves a maximum concentration of ~10$^4$ ng/ml and persists for 7 days, where it is still detectable at ~200 ng/ml (FIG. 3). With subcutaneous administration, the 20 kDa dualPEGylated-leptin bioconjugate achieves a maximum concentration of ~4×10$^3$ ng/ml after ~15 hours and persists at least 6 days (FIG. 4). Together, these data illustrate the extraordinary increase in pharmacokinetic half life in vivo achieved by the dualPEGylated-leptin relative to native rhu-leptin. Furthermore, this bioconjugate appears to have good bioavailability when administered subcutaneously.

EXAMPLE 6

The accumulation of renal vacuoles in the proximal microtubule epithelium has been observed with administration of 20 kDa monoPEGylated-leptin and is dose dependent. Although the doses required to induce vacuolation are well in excess of the therapeutic dose and even severe vacuolation seems to cause no renal dysfunction, this apparent toxicity is considered undesirable. One hypothesis applied in the design of dualPEGylated-leptin was that the dynamic properties of two independent polymers at opposite ends of the leptin molecule may both increase the total hydrodynamic volume of the conjugate and resist collapse of the polymer and thus penetration of the renal microtubules.

Figure 5:
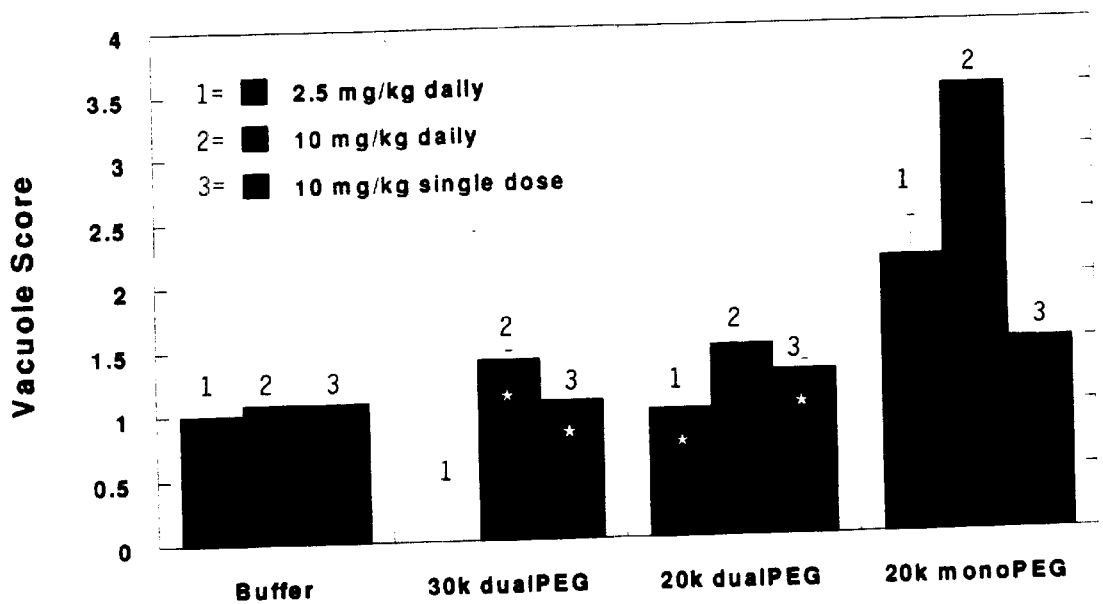
FIG. 5 is a bar graph depicting the kidney vacuole score comparison for various leptin preparations. 1=2.5 mg/kg daily; 2=10 mg/kg daily; 3=10 mg/kg single dose. *=Not statistically significant difference from buffer.

In this study, adult (8–12 week-old) female C57BL/6 mice weighing 18–21g were dosed with either buffer (PBS), 20 kDa monoPEG-leptin, 20 kDa dualPEGylated-leptin or 30 kDa dualPEGylated-leptin. Each preparation was administered by subcutaneous injection of either 2.5 mg/kg/day or 10 mg/kg/day for 7 days or a single 10 mg/kg dose followed by a 7 day recovery period. Three animals from each dosing group were necropsied on day 7 and the kidneys subjected to histological examination to assess the degree of conjugate induced vacuolation. FIG. 5 illustrates a dramatic reduction in the dualPEGylated-leptin's propensity to induce kidney vacuoles relative to the 20 kDa monoPEGylated-leptin control, even at levels 30–45 fold above the efficacious dose. This observation is particularly striking considering that the dualPEGylated-leptin bioconjugates actually deliver 2–3 times the total mass of PEG/dose as the monoPEGylated-leptin conjugate. Further, the extended pharmacokinetics observed with the dualPEGylated-leptin bioconjugates demonstrated in FIGS. 3 & 4 suggests considerable accumulation of these conjugates in a daily dosing scenario relative to the monoPEGylated-leptin conjugate.

EXAMPLE 7

This example describes a study wherein once-a-week dosing regimens were compared for dualPEGylated-leptin vs. monoPEGylated-leptin. Mice were dosed subcutaneously with 25 mg/kg, 10 mg/kg or 2.5 mg/kg of 20 kDa dualPEGylated-leptin or 25 mg/kg or 2.5 mg/kg of 20 kDa monoPEGylated-leptin on days 0, 7, 14 and 21. Weight loss relative to a buffer control was monitored over 44 days.

Figure 6:
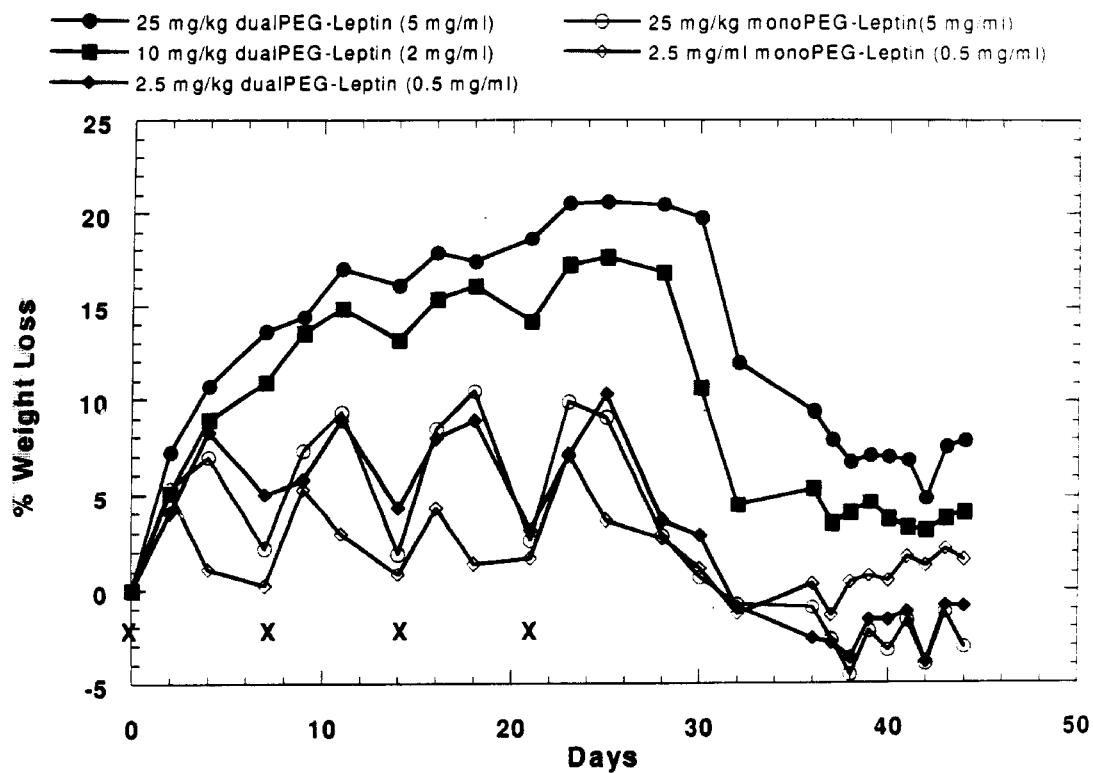
FIG. 6 is a graph depicting % weight loss obtained using various leptin conjugate preparations, at different dosages, following subcutaneous dosing on days 0, 7, 14 and 21 (X). Weight loss relative to a buffer control was monitored over 44 days.

The FIG. 6 data shows an approximate 10-fold dose reduction for the dualPEGylated-leptin relative to monoPEGylated-leptin when applied to a once-a-week dosing regimen. These data are consistent with the pharmacokinetic data presented in FIGS. 3 and 4 and also demonstrate that the dualPEGylated-leptin is capable of inducing and maintaining substantial weight loss (~20%).

EXAMPLE 8

This example describes a study designed to further evaluate kidney pathology associated with dualPEGylated-leptin preparations as compared to monoPEGylated-leptin preparations.

Adult (12-week-old),female C57BL/6 mice weighing 18 to 21 grams received subcutaneous injections of a leptin formulation once weekly for three weeks except for a control group, which received phosphate buffered saline (PBS).

Necropsy was performed the day of the last injection, during which livers and kidneys were examined for gross abnormalities and then immersed in neutral buffered 10% formalin. After fixation, kidneys, livers, lymph nodes, and spleens were dehydrated in graded alcohols, cleared in xylene, and embedded in paraffin. For each organ, one tissue block for three mice from each group were processed together, yielding one section per animal.

Six-μm-thick sections were stained with hematoxylin and eosin (HE), and multiple fields were examined at 40×, 10× and 400× magnifications. The severity of cytoplasmic vacuolar changes in hepatic, lymphatic, and splenic macrophages as well as renal tubular epithelia was graded semi-quantitatively using a five-tiered scale: ±=questionable (very rare, small vacoules in few cells); 1+=minimal (rare, small vacuoles in some cells); 2+=mild (modest numbers of ~3 μm diameter vacuoles); 3+=moderate (large numbers of ~3 μm to ~5 μm diameter vacuoles); or 4+=marked (myriad large >5 μm in diameter, coalescing vacuoles). In rare instances, an equivocal (±) grade was applied if vacuoles were present but exceedingly rare. This scale combines an assessment of lesion severity for individual functioning units (e.g., one renal tubule) with the extent of the lesion within the entire tissue section.

Figure 7:
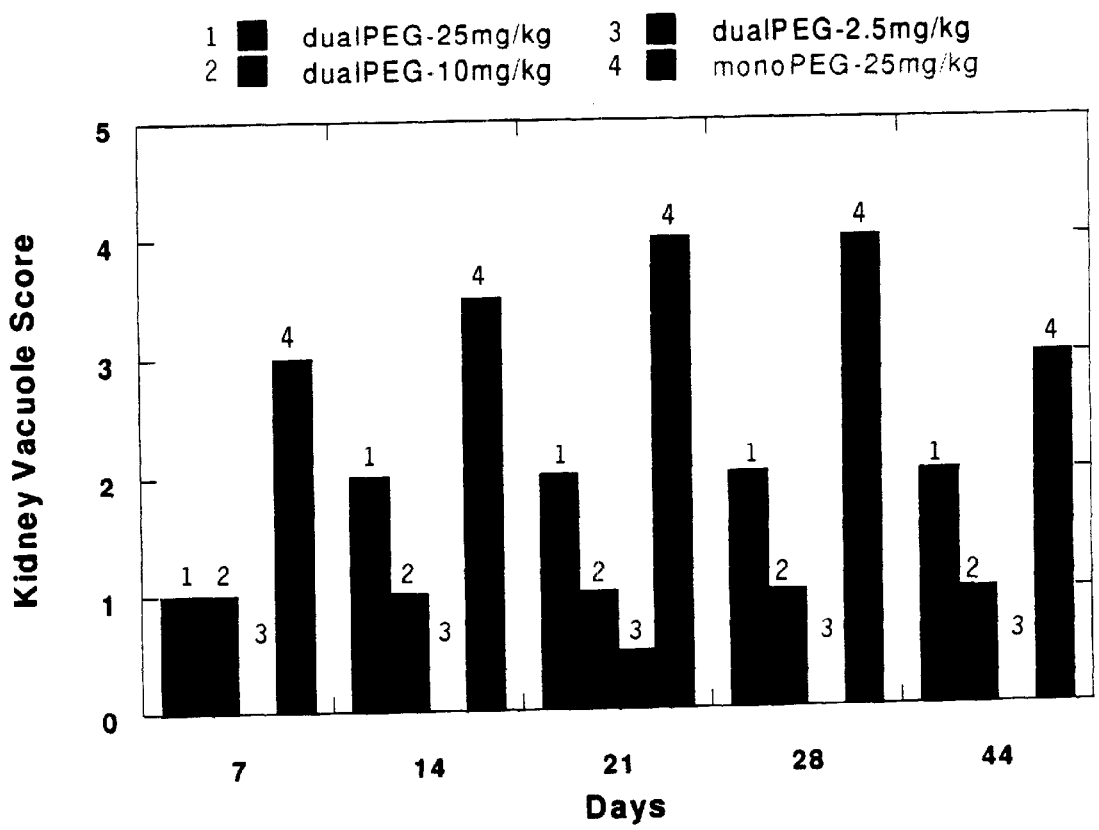
FIG. 7 is a bar graph depicting the kidney vacuole score comparison for various leptin preparations. 1=dualPEGylated (25 mg/kg); 2=dualPEGylated (10 mg/kg); 3=dualPEGylated (2.5 mg/kg); 4=monoPEGylated (25 mg/kg). Kidney Vacuole Score is plotted for each preparation at various time points (# of days).

The results of the study are depicted in FIG. 7. The initial dose of 20 kDa monoPEGylated-leptin (positive control) resulted in a moderate (3+) lesion (consisting of myriad small, clear cytoplasmic vacuoles) in most epithelial cells of many renal proximal tubules. The severity of this change increased to marked (4+) with subsequent injections. After one or three weeks of recovery, renal epithelium contained slightly fewer but much larger vacuoles.

All doses of 20 kDa dualPEGylated-leptin resulted in very minimal (±) to mild (2+) vacuolation in renal proximal tubules at some point during the experiment. During the three-week treatment phase, vacoues generally were small and occurred singly or in pairs within cells, usually in an apical location. Most were located in the supranuclear cytoplasm and were separated from the apical line of tiny vacuoles (presumably endocytotic) that are present in many renal tubular cells as a normal physiological structure. The extent of vacuolation was dose-dependent at all time points. Minimal (1+) numbers of vacuoles were observed for the 10 mg/kg dose at all time points, while a very minimal lesion (±) occurred for the 2.5 mg/kg dose only after the third injection. The mild (2+) class was observed for the 25 mg/kg dose after the second injection and lasted throughout the remainder of the study. The lesion regressed completely within one week at the 2.5 mg/kg dose. At the 10 mg/kg and the 25 mg/kg doses, the number of vacuoles decreased slightly during the recovery phase and the individual vacuoles became larger, suggesting that vacuoles and their contents were consolidated into larger vacuoles or deposits.

The FIG. 7 data demonstrate that dualPEGylated-leptin exhibits significant reduction in kidney vacuole accumulation relative to monoPEGylated-leptin.

None of the leptin compounds (including the positive control material) induced vacuoles in macrophages of the liver, lymph nodes, or spleen of C57BL/6 mice following once weekly administration at 2.5, 10, or 25 mg/kg for three weeks.

What is claimed is:

1. A dualPEGylated-leptin bioconjugate comprising: a polyethylene glycol moiety attached site-specifically to a cysteine residue, said cysteine residue having been engineered into amino acid position 78 (according to the amino acid sequence of SEQ ID NO: 1) within the amino acid sequence of said leptin; and a polyethylene glycol moiety attached site-specifically to the N-terminus of said leptin moiety.

2. The dualPEGylated-leptin bioconjugate of claim 1 wherein said leptin moiety is selected from the group consisting of (according to the amino acid sequence of SEQ ID NO: 1):

(a) the amino acid sequence of SEQ ID NO: 1, optionally lacking a glutaminyl residue at position 28, and further optionally having a methionyl residue at the N-terminus;

(b) an amino acid sequence of subpart (a) having a different amino acid substituted in one or more of the following positions: 4, 8, 32, 33, 35, 48, 50, 53, 60, 64, 66, 67, 68, 71, 74, 77, 78, 89, 97, 100, 102, 105, 106, 107, 108, 111, 112, 118, 136, 138, 142 and 145;

(c) an amino acid sequence of subpart (b) wherein the amino acids at positions 100 and 138 are substituted with Gln;

(d) a truncated leptin protein analog selected from among:
 (i) amino acids 1–99 and 112–146
 (ii) amino acids 1–99 and 112–146 having one or more of amino acids 100–111 sequentially placed between amino acids 99 and 112; and,
 (iii) the truncated leptin analog of subpart (ii) having one or more of amino acids 4, 8, 32, 33, 35, 48, 50, 53, 60, 64, 66, 67, 68, 71, 74, 77, 78, 89, 97, 112, 118, 136, 138, 142 and 145 replaced with another amino acid; and
 (iv) the truncated leptin analog of any of subparts (i)–(iii) having an N-terminal methionyl residue;

(e) a leptin protein of any of subparts (a)–(d) having one or more conserved amino acid substitutions.

3. The dualPEGylated-leptin bioconjugate of claim 1 wherein said polyethylene glycol moieties have a molecular weight from about 20 kDa to about 40 kDa.

4. A pharmaceutical composition comprising a dualPEGylated-leptin bioconjugate according to any of claims 1 to 3 in a pharmaceutically acceptable carrier.

* * * * *